Jan. 4, 1938. L. BURBANK Plant Pat. 266
ROSE
Filed Dec. 9, 1936
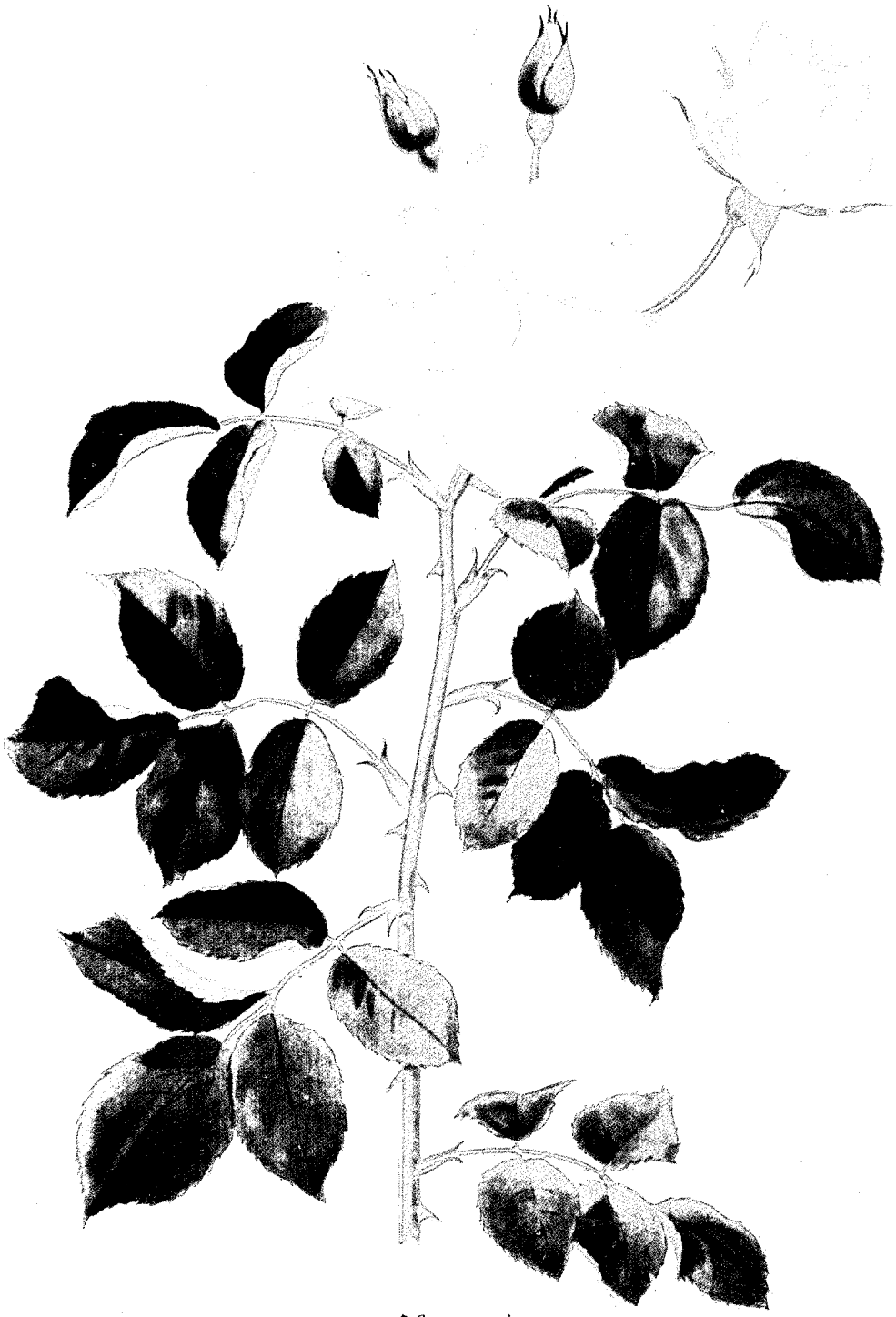
Elizabeth Waters Burbank
Executrix of the estate of Luther Burbank deceased.
By Robb & Robb, attorneys Patented Jan. 4, 1938

Plant Pat. 266

UNITED STATES PATENT OFFICE

266

ROSE

Luther Burbank, deceased, late of Santa Rosa, Calif., by Elizabeth Waters Burbank, executrix, Santa Rosa, Calif., assignor to Stark Bro's Nurseries & Orchards Company, Louisiana, Mo.

Application December 9, 1936, Serial No. 115,039

1 Claim. (Cl. 47—61)

This invention relates to a new and distinct variety of rose plant of the climbing type originating as a seedling of unknown parentage, the novel characteristics of which reside partly in its unique color blending combination and partly in its vigorousness of growth and hardiness, as well as its other features which are referred to hereinafter more specifically.

This new climbing rose, so called, produces a profusion of blossoms in mid-season, its height of bloom in the Burbank Gardens in Santa Rosa, California, being about the middle of May, and in the Mid-West Burbank Gardens early in June.

The buds are medium in size, approximately 1½ inches to two inches at the base and are ovoid in shape.

In color, the bud is grenadine pink tipped with an intermixture of carmine and safrano, having an orange copper effect before the flower opens. The sepals are smooth and straight and the calyx is pear shaped.

The flower of this variety opens well with the outer petals opening first and curling downward, as shown distinctly in the drawing. The general effect, both in color and form, of this new rose is similar to the bush rose known as Countess Vandal.

The blooms are medium to large in size, the largest being approximately 5½ inches and the smallest approximately 3 inches in diameter. They are borne singly, similar to tea roses, and on long stems, such stems being approximately 18 inches in length. The petalage is double to very double. The lasting quality of the bloom is outstanding. It retains its beauty of form for a long period on the plant, and as a cut flower it retains its beauty and form for a long period as compared with hybrid tea roses. The first bloom period is long and every shoot to the ground line produces bloom.

The color of the open rose is rose-dorée, with a tonality from a distance blending of light carmine and yellow with the center of the rose light carmine blended with hermosa pink at base. The bases of the petals inside are deep canary yellow and light canary yellow on the outside. The petals inside are orange pink and on the outside deep safrano pink, a blending of light carmine and yellow. Although the petals hold on for a long time, whorling as they age, they do not dry on the stem, but drop clean. It has a delightful tea-rose fragrance.

The foliage of the new variety is normal in amount and deep green; five leaflets, the end leaflets being approximately 1¼ to 1½ inches; oval-pointed with glossy texture on the upper side and smooth texture on the under side, with medium ribs and veins. Margins are serrated, (single), medium in size and sharp. The plant is very resistant to disease and a vigorous, healthy grower. (Color designations herein referred to are in accordance with Ridgway's color chart), except as to colors not shown therein, in which cases the ordinary dictionary definition is used.

This new rose most closely resembles the climbing rose known as Albertine, but it differs therefrom in many respects among which may be noted the coloring which is entirely distinct from that of Albertine which is coppery pink, while the color effect of this new variety is a combination blending of grenadine pink topped with an intermixture of carmine and safrano and the habit of producing its bloom is entirely different in that this rose produces its bloom singly, like a tea rose, on long, strong stems, while in the cited variety the blooms are produced in loose clusters.

The new variety is much more hardy than Albertine. In an instance of comparative test, the Albertine variety was frozen to the ground under low winter temperatures, while the present variety subject to even more severe cold, came through and produced blooms.

The characteristics which are hereinbefore referred to appear to be fixed according to the results of asexual reproduction of this new variety.

Having thus described this rose, what is claimed as new is:

A new and distinct variety of climbing rose plant, characterized as to novelty by its unusual coloring, its vigorous growth and hardiness, substantially as shown and described.

ELIZABETH WATERS BURBANK,
*Executrix of the Estate of Luther Burbank, Deceased.*